(12) United States Patent
Zarras et al.

(10) Patent No.: US 9,058,915 B1
(45) Date of Patent: Jun. 16, 2015

(54) OMNICONJUGATED CONDUCTIVE POLYMERS AND METHODS FOR MAKING THE SAME

(71) Applicant: The United States of America as represented by the Secretary of the Navy, Washington, DC (US)

(72) Inventors: Peter Zarras, Ridgecrest, CA (US); Alfred Baca, Ridgecrest, CA (US); John D. Stenger-Smith, Ridgecrest, CA (US); Andrew P. Chafin, Ridgecrest, CA (US); William Lai, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 242 days.

(21) Appl. No.: 13/862,609

(22) Filed: Apr. 15, 2013

Related U.S. Application Data

(60) Provisional application No. 61/640,976, filed on May 1, 2012, provisional application No. 61/647,664, filed on May 16, 2012.

(51) Int. Cl.
| | |
|---|---|
| *H01B 1/00* | (2006.01) |
| *C07C 13/00* | (2006.01) |
| *C07D 333/00* | (2006.01) |
| *C07D 339/00* | (2006.01) |
| *H01B 1/12* | (2006.01) |
| *C09D 5/24* | (2006.01) |
| *C08G 73/06* | (2006.01) |
| *C25B 3/00* | (2006.01) |
| *C07C 13/28* | (2006.01) |
| *C07D 339/02* | (2006.01) |

(52) U.S. Cl.
CPC ........ *H01B 1/124* (2013.01); *C09D 5/24* (2013.01); *C08G 73/0611* (2013.01); *C25B 3/00* (2013.01); *C07C 13/28* (2013.01); *C07D 333/00* (2013.01); *C07D 339/02* (2013.01)

(58) Field of Classification Search
CPC .... H01B 1/124; H01L 51/0034; C07C 13/28; C07C 13/32; C07C 13/39; C07C 2102/42; C08G 2261/148; C08G 2261/149; C08G 61/00; C08G 61/10; C07D 333/00; C07D 339/02

See application file for complete search history.

(56) References Cited

U.S. PATENT DOCUMENTS

| | | | | |
|---|---|---|---|---|
| 4,249,013 | A | * | 2/1981 | Haddon et al. ................ 549/35 |
| 4,312,992 | A | * | 1/1982 | Green ............................. 549/59 |
| 4,578,220 | A | * | 3/1986 | Huenig et al. .................. 549/32 |

OTHER PUBLICATIONS

Benet-Buchholz et al "Structural chemistry of dienes and polyenes", The Chemistry of Dienes and Polyenes, vol. 1, Chapter 2 pp. 25-65 1997.*

* cited by examiner

*Primary Examiner* — Mark Kopec
(74) *Attorney, Agent, or Firm* — Charlene A. Haley

(57) ABSTRACT

A new class of polymers based upon the radialene group as the parent repeating group and characterized by the following general formula:

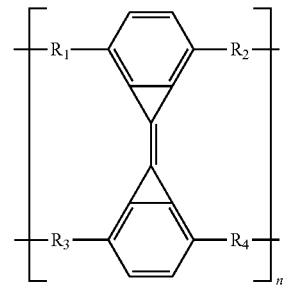

where R1, R2, R3, R4 are each independently any pi electron conjugated group, but not limited to: pyrrole, thiophene, benzene, naphthalene, furan, ethene, aniline, and n is an integer from 2 to 20,000. Furthermore, the individual R groups can be further functionalized with an alky group having 1 to 22 carbons; alkoxy group having 1 to 22 carbons; alkyl sulfonate having 1 to 22 carbons; alkyl phosphate group containing 1 to 22 carbons, alkoxy phosphate group having 1 to 22 carbons; ethenylendioxy group; propylene dioxy group.

12 Claims, No Drawings

OMNICONJUGATED CONDUCTIVE POLYMERS AND METHODS FOR MAKING THE SAME

CROSS-REFERENCE TO RELATED APPLICATIONS

This is a non-provisional patent application, claiming the benefit of, parent application Ser. No. 61/640,976 filed on May 1, 2012 and Ser. No. 61/647,664 filed on May 16, 2012, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to polymers, and more particularly, to new fully pi-conjugated (omniconjugated) conductive molecules that exhibit significantly improved conductivities. This provides the Navy with a novel class of low or zero bandgap polymers that can be incorporated into a variety of devices and coatings as well as of coating and/or paints for corrosion protection of Navy equipment and/or any equipment that might benefit from corrosion inhibiting coatings.

DETAILED DESCRIPTION OF EMBODIMENTS OF THE INVENTION

Conductive polymer (CPs) that can be easily processed into flexible, highly conductive (>>10,000 S/cm) films or devices has been identified as an area of immediate concern to the war fighter for improved communications, improved networking, and new architectural frameworks for naval warfare in the information age.

For over 30 years there has been significant research and commercial interest in CPs. Most CPs are derivatives of acetylene, pyrrole, phenylene vinylenes, thiophenes, and other similar molecules. The conductivities of these materials are normally in the range of 0.01-100 S/cm in ambient atmosphere. In doped CPs, the conductivity is considerably lower than that of metals. In those isolated cases where the conductivity of doped CPs approaches that of metals, such as polyacetylene, they are stable only in an inert atmosphere. Metals are inherently conductive, in which the valence and conduction bands form a single overlapping band allowing for ease of electron mobility. Scientists have spent the past decade devising synthetic strategies to produce CPs with low or zero-bandgaps (Eg<1.5 eV). The concept of a low bandgap polymer would increase the top of the conduction band (HOMO) and a concurrent decrease in the bottom of the valence band (LUMO). With an increase in the HOMO there would be ease of oxidation. However, to date there are no stable low bandgap polymers with the exception of poly (ethylenedioxythiophene, PEDOT, Eg=1.6 eV). The critical need for low or zero bandgap CPs requires that these proposed materials have Eg values<1.5 eV. By incorporating radielene groups into the polymer backbone this will enforce planarity eliminating steric crowding, thereby lowering the bandgap. As a result of lowering the bandgap, an increase in conductivity and ease of oxidation should occur. For future naval applications, bandgap values of <1.5 eV could be obtained and the materials would remain stable under ambient conditions. By providing a planar structure free from the defects that current CPs have which limit their conductivities, a new generation of high CP materials can be realized. These omniconjugated polymers will be polymerized through four terminals producing a polymer backbone that is locked in a planar configuration, allowing for both inter- and intra-electron hopping, significantly improving conductivities (>>10,000 S/cm).

CPs have been extensively investigated for their corrosion inhibiting properties and have been commercialized for industrial use as corrosion inhibitors on steel structures. For ferrous alloys the corrosion protection mechanism has been determined to be via an anodic protection mechanism (passivation) for stainless steels and via released dopant ions for mild steels. For non-ferrous alloys such as, for example, aluminum, several proposed mechanisms have been described. The) include, ennobling of the alloys, thereby minimizing oxygen and hydrogen ion reduction on the metal surface, anodic protection/passivation, galvanic and ion-exchange release of oxygen reduction inhibitors, and barrier protection by the reduced form of the polymer following initial galvanic coupling. By employing a novel corrosion inhibiting polymer coating, this will significantly extend the lifetimes of Navy equipment/aircraft while reducing the costs of maintenance and replacement.

The approach is to synthesize new monomers that can be polymerized via chemical or electrochemical methods that exhibit high conductivities. The approach will be based on the successful synthesis of a stable derivative of triafulvalene including the [3] radialene structure within the molecule. The synthesis described below will incorporate [3] radialenes into stable structures for controlled polymerization producing four terminal molecular interconnects for fully conjugated CPs.

The above objects are achieved according to the invention by the provision of a class of polymers based upon the radialene group as the parent repeating group and characterized by the following general formula:

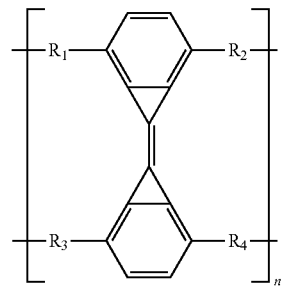

where R1, R2, R3, R4 are each independently pi electron conjugated group, but not limited to: pyrrole, thiophene, benzene, naphthalene, furan, ethene, aniline, and n is an integer from 2 to 20,000. Furthermore, the individual R groups can be further functionalized with an alky group having 1 to 22 carbons; alkoxy group having 1 to 22 carbons; alkyl sulfonate having 1 to 22 carbons; alkyl phosphate group containing 1 to 22 carbons, alkoxy phosphate group having 1 to 22 carbons; ethenylendioxy group; propylene dioxy group.

A variety class of embodiments of the invention has N-methyl pyrrole as the R1-R4 groups, the repeating unit characterizing the polymer shown below.

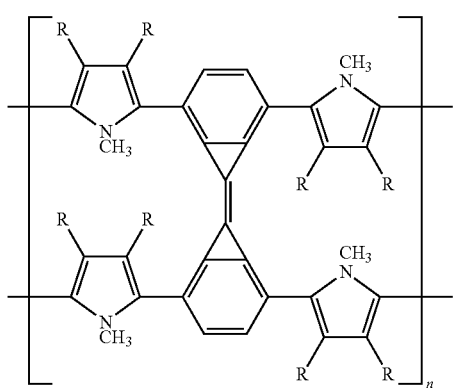

Where R is hydrogen; an alkyl group having 1 to 22 carbons; alkoxy group having 1 to 22 carbons; alkyl sulfonate having 1 to 22 carbons; alkyl phosphate group containing 1 to 22 carbons, alkoxy phosphate group having 1 to 22 carbons; ethenylendioxy group; propylene dioxy group.

Another embodiment of the variety class of this invention has thiophene as the R1-R4 groups, the repeating unit characterizing the polymer shown below

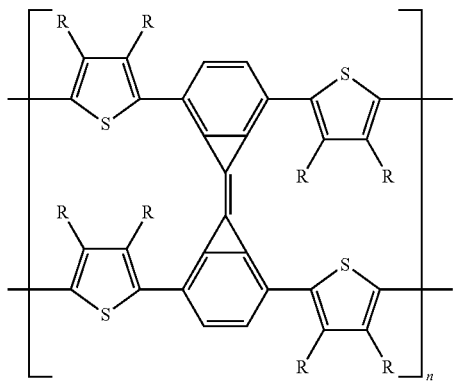

Where R is hydrogen; an alkyl group having 1 to 22 carbons; alkoxy group having 1 to 22 carbons; alkyl sulfonate having 1 to 22 carbons; alkyl phosphate group containing 1 to 22 carbons, alkoxy phosphate group having 1 to 22 carbons; ethenylendioxy group; propylene dioxy group.

Yet another embodiment of the variety class of this invention has phenylene vinylene as the R1-R4 groups, the repeating unit characterizing the polymer shown below

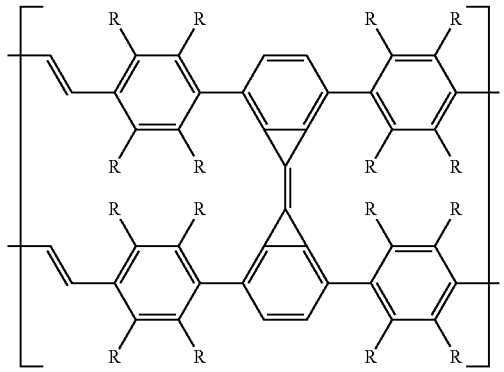

Where R is hydrogen; an alkyl group having 1 to 22 carbons; alkoxy group having 1 to 22 carbons; alkyl sulfonate having 1 to 22 carbons; alkyl phosphate group containing 1 to 22 carbons, alkoxy phosphate group having 1 to 22 carbons.

Yet more embodiments of the variety classes have R1-R4 group as benzene, naphthalene, furan, and aniline.

Films of the above class of polymers can be formed from casting from a solvent solution, electrochemically deposited onto a substrate, with the films exhibiting high conductivities and/or corrosion inhibiting properties. Powders of the above listed polymers can be pressed into pellets or mixed with other polymeric materials to form films with high conductivities and/or corrosion inhibiting properties.

EXAMPLES

The synthesis of an omniconjugated polymer (see Scheme 1) starts with as an example N-methylpyrrole (commercially available from Aldrich Chemicals) and reaction dimethyl ammonium hydrochloride and formaldehyde, followed by treatment with methyl iodide and ethanol. The resulting pyrrole-2-yl methanaminium iodide 1 is further reacted with triphenyl phosphine to give (1-methyl-1-H-pyrrol-2-yl methyl)triphenylphosphonium iodide, which is used in a later step. N-methylpyrrole is treated with an amino acrylaldehyde in the presence of phosphorous oxychloride to form the pyrrole-2-yl acrylaldehyde. This acrylaldehyde and the previously made triphenylphosphonium iodide derivative are reacted with base to form (1E,3E)-1,4-bis(1-methyl-1H-pyrrol-2-yl) buta-1,3-diene. This butadiene derivative is then reacted with 1,2,3,3 tetrachloro cyclopropene followed by treatment with Potassium t-butoxide and then N-butyl lithium to make the monomer (Monomer 1). Monomer 1 can be electropolymerized or chemical oxidation to produce an omniconjugated polymer structure. The synthetic approaches outlined in the scheme represent a reasonable and readily obtainable method for producing fully pi-conjugated conductive polymers. Other conjugated groups such as thiophene, benzene, naphthalene, furan, ethene, and aniline can be used in the place of pyrrole, as well as the appropriately substituted conjugated groups. When the monomers are characterized and polymerized, conductivities, redox and thermal properties of these new conductive polymer structures will be determined to evaluate the robustness of this new type of CP.

Scheme 1: Synthesis pathway to an omniconjugated polymer.

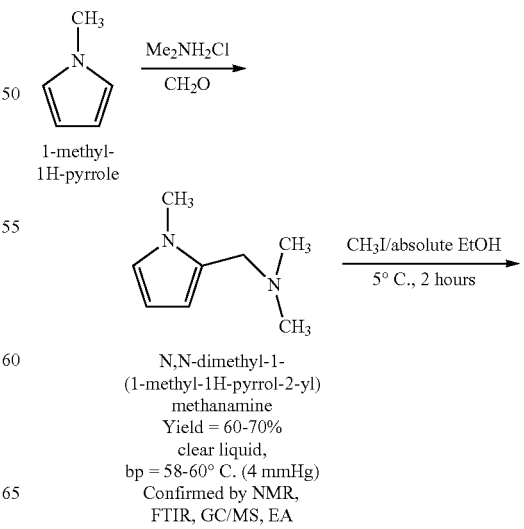

5
-continued

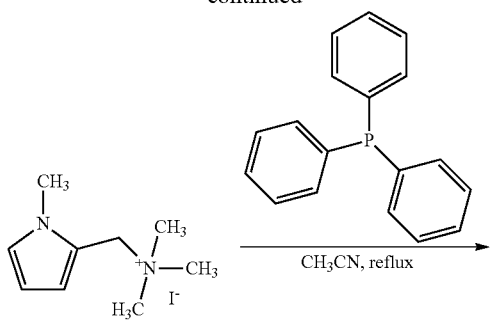

N,N,N-trimethyl-1-
(1-methyl-1H-pyrrol-2-yl)
methanaminium iodide
Yield = ~95-98%
white cystals
Confirmed by NMR,
FTIR, ESI-MS
Scale-up >50 grams ((1-methyl-1H-pyrrol-2-yl)methyl)
triphenylphosphonium
Yield = ~75-85%
off-white powder
Confirmed by NMR, FTIR, ESI-MS
Scale-up >50 grams

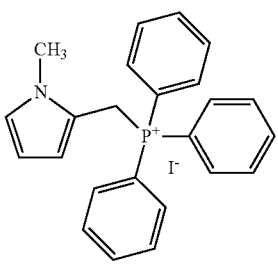

1-methyl-1H-
pyrrole 3-(dimethylamino)acrylaldehyde (E)-3-(1-methyl-1H-pyrrol-2-yl)
acrylaldehyde
Yield = ~40%,
red-brown needles
Confirmed by NMR, GC/MS,
FTIR, EA
Scale-up >25 grams

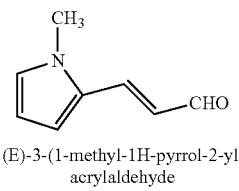

(E)-3-(1-methyl-1H-pyrrol-2-yl)
acrylaldehyde

6
-continued

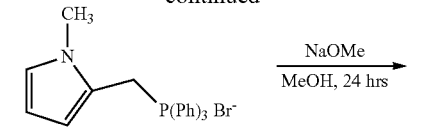

1-methyl-1H-pyrrol-2-yl)methyl-
triphenylphosphonium iodide

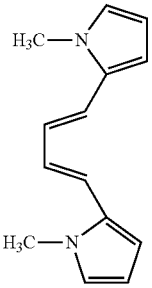

(1E,3E)-1,4-bis
(1-methyl-1H-pyrrol-2-yl)
buta-1,3-diene
Yield of crude material = 57%,
orange-browm powder
impurity present confirmed by
NMR and GC/MS

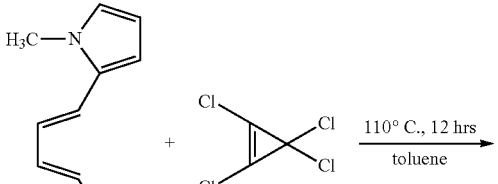

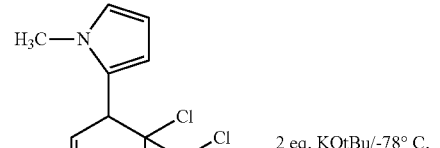

2,2'-(1,6,7,7-tetrachlorobicyclo
[4.1.0]-hept-3-ene-2,5-diyl)bis
(1-methyl-1H-pyrrole)

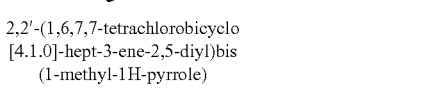
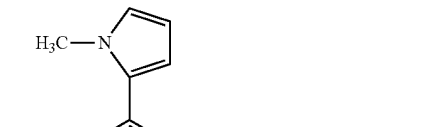
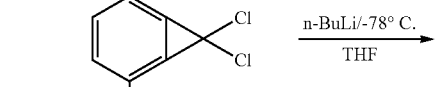

2,2'-(1,1-dichloro-1H-cyclopropa-
benzene-2,5-diyl)bis
(1-methyl-1H-pyrrole)

-continued

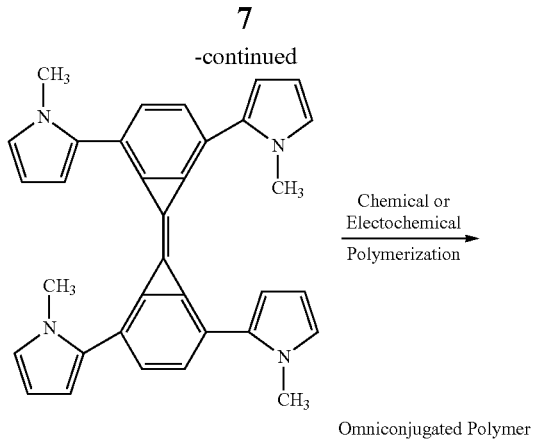

Chemical or Electochemical Polymerization

Omniconjugated Polymer

Additional omniconjugated monomers can be constructed with adhesion promoting groups and for water-dispersible systems (formulations). Once the monomers are characterized, they will be polymerized via oxidative polymerization methods to produce high molecular weight polymers. They will be dissolved in the appropriate VOC-exempt (such as 3-chlorobenzotrifluoride also known by its trade name Oxsol-100) or formulated in a water-dispersible system for spray applications using HVLP apparatus. Concurrently with the oxidative polymerization method, electropolymerization of the monomers directly onto metal substrates can also be performed. Both methods will provide a pathway to produce dense, pin-hole free coatings onto a metal substrate. Their corrosion inhibiting properties on metal alloys using a combination of accelerated weathering, adhesion and electrochemical tests will be performed.

The tests will include: neutral salt fog exposure (ASTM B 117), GM 9540P cabinet testing, natural marine atmosphere exposure testing at the NSWCCD's corrosion test site, Ft. Lauderdale, Fla. (ASTM D 1014), and dry and wet-tape adhesion tests (ASTM D 3359). The tests will determine whether the materials can adhere onto metal alloys and meet corrosion performance requirements for DON environments. Mechanistic studies will be performed by using a combination of electrochemical, spectroscopic methods (EIS, SVET, galvanic coupling measurements, SEM-EDXA, XPS and MFX) for determination of cathodic protection. Each of the electrochemical and spectroscopic techniques will provide quantitative evidence that the newly developed omniconjugated polymers can inhibit corrosion through a cathodic corrosion mechanism.

Embodiments of the invention generally relate to methods for synthesizing omniconjugated polymers including, reacting at least one pi conjugated group with an alkyl ammonium hydrochloride and an aldehyde, treating the reacted first conjugated groups with alkyl halide and an alcohol producing conjugated alkylanaminium halide, reacting the alkylanaminium halide with triphenyl phosphine to produce a conjugated-yl triphenylphosphonium halide, treating a second conjugated group with an amino acrylaldehyde in the presence of an oxidizing agent to produce conjugated-yl acrylaldehyde, reacting the acrylaldehyde and the triphenylphosphonium halide derivative with base to produce (1E,3E)-1,4-bis(l-conjugated-yl) buta-1,3-diene, reacting the butadiene derivative with 1,2,3,3 tetrachlorocyclopropene and treating with base and with N-alkyllithium to produce the monomer, and electropolymerizing or chemically oxidizing the monomer to produce an omniconjugated polymer structure.

In embodiments, the either the first and/or second conjugated group is pi conjugated group. In other embodiments, either the first and/or second conjugated group is independently selected from the group consisting of N-methylpyrrole, pyrrole, thiophene, benzene, naphthalene, furan, ethene, and aniline. Embodiments of the invention further include casting the omniconjugated polymers from a solvent solution and electrochemically depositing onto a substrate forming a film. Embodiments of the invention further include pressing the omniconjugated polymer powders into pellets or mixed with other polymeric materials. Embodiments of the invention further include doping and electrically conducting said omniconjugated polymers. Another aspect of the invention generally relates to omniconjugated polymers produced by the methods herein.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed:
1. An omniconjugated polymer having singular independent repeating units, comprising of general formula 1:

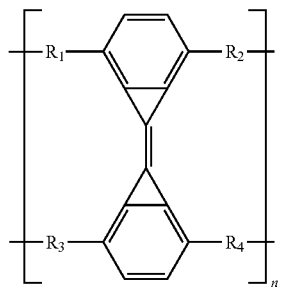

wherein R1, R2, R3, R4 are each pi conjugated group independently selected from the group consisting of N-methylpyrrole, pyrrole, thiophene, benzene, naphthalene, furan, ethene, aniline; wherein each said conjugated group optionally having at least one R is independently selected from the group consisting of hydrogen; alkyl group having 1 to 22 carbons; alkoxy group having 1 to 22 carbons; alkyl sulfonate having 1 to 22 carbons; alkyl phosphate group having 1 to 22 carbons, alkoxy phosphate group having 1 to 22 carbons; ethenylendioxy group; propylene dioxy group (general formula 2, 3, 4); and
wherein n is an integer from 2 to 20,000.
2. The omniconjugated polymer according to claim 1, wherein said general formula 1 comprises,

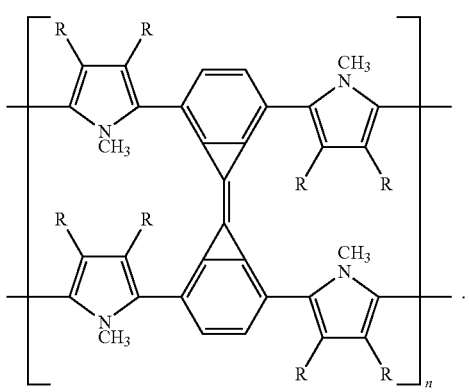

3. The omniconjugated polymer according to claim 1, wherein said general formula 1 comprises, Formula 2

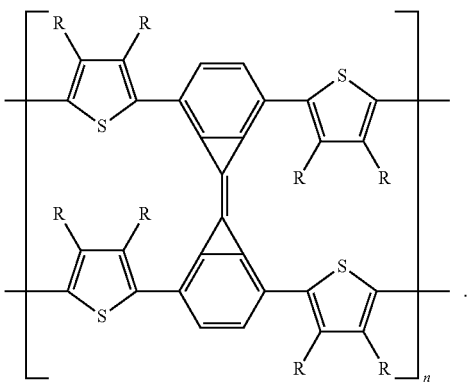

4. The omniconjugated polymer according to claim 1, wherein said general formula 1 comprises, Formula 3

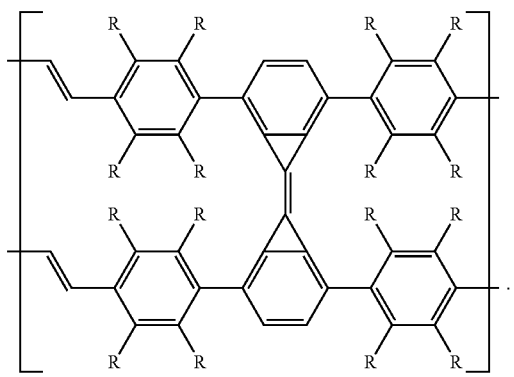

5. The polymer according to claim 1, wherein said omniconjugated polymer having an average molecular weight from about 600 to about 2,000,000 g/mole.

6. A method for synthesizing omniconjugated polymers, comprising:
   reacting at least one pi conjugated group with an alkyl ammonium hydrochloride and an aldehyde;
   treating said reacted first conjugated groups with alkyl halide and an alcohol producing conjugated alkylanaminium halide;
   reacting said alkylanaminium halide with triphenyl phosphine to produce a conjugated-yl triphenylphosphonium halide;
   treating a second conjugated group with an amino acrylaldehyde in the presence of an oxidizing agent to produce conjugated-yl acrylaldehyde;
   reacting said acrylaldehyde and said triphenylphosphonium halide derivative with base to produce (1E,3E)-1, 4-bis(1-conjugated-yl) buta-1,3-diene;
   reacting said butadiene derivative with 1,2,3,3 tetrachlorocyclopropene and treating with base and with N-alkyl-lithium to produce the monomer; and
   electropolymerizing or chemically oxidizing said monomer to produce an omniconjugated polymer structure.

7. The methods according to claim 6, wherein either said first and/or second conjugated group is pi conjugated group.

8. The methods according to claim 6, wherein either said first and/or second conjugated group is independently selected from the group consisting of N-methylpyrrole, pyrrole, thiophene, benzene, naphthalene, furan, ethene, and aniline.

9. The methods according to claim 6, further comprising casting said omniconjugated polymers from a solvent solution and electrochemically depositing onto a substrate forming a film.

10. The methods according to claim 6, further comprising pressing said omniconjugated polymer powders into pellets or mixed with other polymeric materials.

11. The methods according to claim 6, further comprising doping and electrically conducting said omniconjugated polymers.

12. Omniconjugated polymers produced by the methods of claim 6.

* * * * *